(12) United States Patent
Franer et al.

(10) Patent No.: US 9,241,758 B2
(45) Date of Patent: Jan. 26, 2016

(54) SURGICAL INSTRUMENT WITH BLADE COMPLIANT ALONG VERTICAL CUTTING EDGE PLANE

(71) Applicant: Ethicon Endo-Surgery, Inc., Cincinnati, OH (US)

(72) Inventors: Paul T. Franer, Cincinnati, OH (US); Zhifan F. Huang, Mason, OH (US); Jerome R. Morgan, Cincinnati, OH (US); Frederick E. Shelton, IV, Hillsboro, OH (US); Bret W. Smith, Kings Mills, OH (US); Richard W. Timm, Cincinnati, OH (US); Gregory A. Trees, Loveland, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 15 days.

(21) Appl. No.: 13/749,877

(22) Filed: Jan. 25, 2013

(65) Prior Publication Data
US 2014/0214029 A1   Jul. 31, 2014

(51) Int. Cl.
*A61B 18/00* (2006.01)
*A61B 18/14* (2006.01)
*A61B 19/00* (2006.01)

(52) U.S. Cl.
CPC ......... *A61B 18/1445* (2013.01); *A61B 18/1447* (2013.01); *A61B 2018/00196* (2013.01); *A61B 2018/00607* (2013.01); *A61B 2018/1455* (2013.01); *A61B 2019/304* (2013.01)

(58) Field of Classification Search
CPC ........... A61B 18/1442; A61B 18/1445; A61B 2017/07285
USPC .................................. 606/50–52, 205–211
See application file for complete search history.

(56) References Cited

U.S. PATENT DOCUMENTS

| | | | |
|---|---|---|---|
| 5,865,361 A * | 2/1999 | Milliman et al. | ..... 227/176.1 |
| 6,500,176 B1 | 12/2002 | Truckai et al. | |
| 6,783,524 B2 | 8/2004 | Anderson et al. | |
| 7,112,201 B2 | 9/2006 | Truckai et al. | |
| 7,125,409 B2 | 10/2006 | Truckai et al. | |
| 7,169,146 B2 | 1/2007 | Truckai et al. | |
| 7,186,253 B2 | 3/2007 | Truckai et al. | |
| 7,189,233 B2 | 3/2007 | Truckai et al. | |
| 7,220,951 B2 | 5/2007 | Truckai et al. | |

(Continued)

OTHER PUBLICATIONS

U.S. Appl. No. 13/692,202, filed Dec. 3, 2012.

(Continued)

*Primary Examiner* — Joseph Stoklosa
*Assistant Examiner* — Jocelyn D Ram
(74) *Attorney, Agent, or Firm* — Frost Brown Todd LLC (57) ABSTRACT

An apparatus comprises a body, a shaft, an end effector, and a firing beam. The shaft extends distally from the body. The end effector is positioned at the distal end of the shaft. The end effector comprises a first jaw and a second jaw, with the first jaw being pivotable toward the second jaw. The firing beam is operable to translate relative to the end effector to thereby drive the first jaw toward the second jaw. The firing beam includes a deformable portion operable to deform in response to a stress imposed by the end effector on the firing beam as the jaws clamp on dense or thick tissue. The deformable portion is defined in part by a cutout. A compliance restriction feature restricts deformation in the firing beam. A resilient member biases the firing beam to a non-deformed configuration.

16 Claims, 8 Drawing Sheets

(56) References Cited

U.S. PATENT DOCUMENTS

| | | | |
|---|---|---|---|
| 7,287,682 B1* | 10/2007 | Ezzat et al. | 227/175.1 |
| 7,309,849 B2 | 12/2007 | Truckai et al. | |
| 7,311,709 B2 | 12/2007 | Truckai et al. | |
| 7,354,440 B2 | 4/2008 | Truckai et al. | |
| 7,381,209 B2 | 6/2008 | Truckai et al. | |
| 7,434,717 B2* | 10/2008 | Shelton et al. | 227/176.1 |
| 7,441,684 B2* | 10/2008 | Shelton et al. | 227/175.1 |
| 7,472,815 B2* | 1/2009 | Shelton et al. | 227/176.1 |
| 7,500,979 B2* | 3/2009 | Hueil et al. | 606/139 |
| 7,543,730 B1* | 6/2009 | Marczyk | 227/175.1 |
| 8,277,446 B2 | 10/2012 | Heard | |
| 8,409,246 B2 | 4/2013 | Kerr et al. | |
| 8,460,292 B2* | 6/2013 | Truckai et al. | 606/51 |
| 8,469,254 B2* | 6/2013 | Czernik et al. | 227/176.1 |
| 2002/0165541 A1* | 11/2002 | Whitman | 606/48 |
| 2003/0114851 A1* | 6/2003 | Truckai | A61B 18/1445 606/51 |
| 2008/0078800 A1* | 4/2008 | Hess et al. | 227/175.1 |
| 2008/0083809 A1* | 4/2008 | Scirica | 227/175.1 |
| 2008/0308605 A1* | 12/2008 | Scirica | 227/175.1 |
| 2009/0206134 A1* | 8/2009 | Swayze et al. | 227/176.1 |
| 2010/0072258 A1* | 3/2010 | Farascioni et al. | 227/180.1 |
| 2010/0181364 A1* | 7/2010 | Shelton et al. | 227/180.1 |
| 2010/0274244 A1* | 10/2010 | Heard | A61B 18/1442 606/45 |
| 2011/0087218 A1 | 4/2011 | Boudreaux et al. | |
| 2011/0108605 A1* | 5/2011 | Sapienza | 227/180.1 |
| 2011/0132964 A1* | 6/2011 | Weisenburgh et al. | 227/176.1 |
| 2011/0180585 A1* | 7/2011 | Czernik | A61B 17/07207 227/176.1 |
| 2011/0306968 A1* | 12/2011 | Beckman | A61B 18/1482 606/41 |
| 2012/0078243 A1 | 3/2012 | Worrell et al. | |
| 2012/0078244 A1 | 3/2012 | Worrell et al. | |
| 2012/0078247 A1 | 3/2012 | Worrell et al. | |
| 2012/0078248 A1 | 3/2012 | Worrell et al. | |
| 2012/0116379 A1 | 5/2012 | Yates et al. | |
| 2013/0023868 A1 | 1/2013 | Worrell et al. | |
| 2013/0030428 A1 | 1/2013 | Worrell et al. | |
| 2014/0336698 A1* | 11/2014 | Boudreaux et al. | 606/206 |

OTHER PUBLICATIONS

U.S. Appl. No. 61/410,603, filed Nov. 5, 2010.
International Search Report dated Apr. 10, 2014 for Application No. PCT/US2014/011595.
International Written Opinion dated Apr. 10, 2014 for Application No. PCT/US2014/011595.

* cited by examiner

SURGICAL INSTRUMENT WITH BLADE COMPLIANT ALONG VERTICAL CUTTING EDGE PLANE

BACKGROUND

A variety of surgical instruments include a tissue cutting element and one or more elements that transmit RF energy to tissue (e.g., to coagulate or seal the tissue). An example of such a device is the ENSEAL® Tissue Sealing Device by Ethicon Endo-Surgery, Inc., of Cincinnati, Ohio. Further examples of such devices and related concepts are disclosed in U.S. Pat. No. 6,500,176 entitled "Electrosurgical Systems and Techniques for Sealing Tissue," issued Dec. 31, 2002, the disclosure of which is incorporated by reference herein; U.S. Pat. No. 7,112,201 entitled "Electrosurgical Instrument and Method of Use," issued Sep. 26, 2006, the disclosure of which is incorporated by reference herein; U.S. Pat. No. 7,125,409, entitled "Electrosurgical Working End for Controlled Energy Delivery," issued Oct. 24, 2006, the disclosure of which is incorporated by reference herein; U.S. Pat. No. 7,169,146 entitled "Electrosurgical Probe and Method of Use," issued Jan. 30, 2007, the disclosure of which is incorporated by reference herein; U.S. Pat. No. 7,186,253, entitled "Electrosurgical Jaw Structure for Controlled Energy Delivery," issued Mar. 6, 2007, the disclosure of which is incorporated by reference herein; U.S. Pat. No. 7,189,233, entitled "Electrosurgical Instrument," issued Mar. 13, 2007, the disclosure of which is incorporated by reference herein; U.S. Pat. No. 7,220,951, entitled "Surgical Sealing Surfaces and Methods of Use," issued May 22, 2007, the disclosure of which is incorporated by reference herein; U.S. Pat. No. 7,309,849, entitled "Polymer Compositions Exhibiting a PTC Property and Methods of Fabrication," issued Dec. 18, 2007, the disclosure of which is incorporated by reference herein; U.S. Pat. No. 7,311,709, entitled "Electrosurgical Instrument and Method of Use," issued Dec. 25, 2007, the disclosure of which is incorporated by reference herein; U.S. Pat. No. 7,354,440, entitled "Electrosurgical Instrument and Method of Use," issued Apr. 8, 2008, the disclosure of which is incorporated by reference herein; U.S. Pat. No. 7,381,209, entitled "Electrosurgical Instrument," issued Jun. 3, 2008, the disclosure of which is incorporated by reference herein.

Additional examples of electrosurgical cutting instruments and related concepts are disclosed in U.S. Pub. No. 2011/0087218, entitled "Surgical Instrument Comprising First and Second Drive Systems Actuatable by a Common Trigger Mechanism," published Apr. 14, 2011, now U.S. Pat. No. 8,939,974, issued Jan. 27, 2015, the disclosure of which is incorporated by reference herein; U.S. Pub. No. 2012/0116379, entitled "Motor Driven Electrosurgical Device with Mechanical and Electrical Feedback," published May 10, 2012, now U.S. Pat. No. 9,161,803, issued Oct. 20, 2015, the disclosure of which is incorporated by reference herein; U.S. Pub. No. 2012/0078243, entitled "Control Features for Articulating Surgical Device," published Mar. 29, 2012, the disclosure of which is incorporated by reference herein; U.S. Pub. No. 2012/0078247, entitled "Articulation Joint Features for Articulating Surgical Device," published Mar. 29, 2012, the disclosure of which is incorporated by reference herein; U.S. patent application Ser. No. 13/622,729, entitled "Surgical Instrument with Multi-Phase Trigger Bias," filed Sep. 19, 2012, now U.S. Pat. No. 9,089,327, issued Jul. 28, 2015, the disclosure of which is incorporated by reference herein; and U.S. patent application Ser. No. 13/622,735, entitled "Surgical Instrument with Contained Dual Helix Actuator Assembly," filed Sep. 19, 2012, now U.S. Pub. No. 2013/0023868, published Jan. 24, 2013, the disclosure of which is incorporated by reference herein.

While several medical devices have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Electrosurgical Device with Articulation Feature

FIGS. 1-4 show an exemplary electrosurgical instrument (10) that is constructed and operable in accordance with at least some of the teachings of U.S. Pat. No. 6,500,176; U.S. Pat. No. 7,112,201; U.S. Pat. No. 7,125,409; U.S. Pat. No. 7,169,146; U.S. Pat. No. 7,186,253; U.S. Pat. No. 7,189,233; U.S. Pat. No. 7,220,951; U.S. Pat. No. 7,309,849; U.S. Pat. No. 7,311,709; U.S. Pat. No. 7,354,440; U.S. Pat. No. 7,381,209; U.S. Pub. No. 2011/0087218, now U.S. Pat. No. 8,939,974; U.S. Pub. No. 2012/0116379, now U.S. Pat. No. 9,161,803; U.S. Pub. No. 2012/0078243; U.S. Pub. No. 2012/0078247; U.S. patent application Ser. No. 13/622,729, now U.S. Pat. No. 9,089,327; and/or U.S. patent application Ser. No. 13/622,735, now U.S. Pub. No. 2013/0023868. As described therein and as will be described in greater detail below, electrosurgical instrument (10) is operable to cut tissue and seal or weld tissue (e.g., a blood vessel, etc.) substantially simultaneously. In other words, electrosurgical instrument (10) operates similar to an endocutter type of stapler, except that electrosurgical instrument (10) provides tissue welding through application of bipolar RF energy instead of providing lines of staples to join tissue. It should also be understood that electrosurgical instrument (10) may have various structural and functional similarities with the ENSEAL® Tissue Sealing Device by Ethicon Endo-Surgery, Inc., of Cincinnati, Ohio. Furthermore, electrosurgical instrument (10) may have various structural and functional similarities with the devices taught in any of the other references that are cited and incorporated by reference herein. To the extent that there is some degree of overlap between the teachings of the references cited herein, the ENSEAL® Tissue Sealing Device by Ethicon Endo-Surgery, Inc., of Cincinnati, Ohio, and the following teachings relating to electrosurgical instrument (10), there is no intent for any of the description herein to be presumed as admitted prior art. Several teachings below will in fact go beyond the scope of the teachings of the references cited herein and the ENSEAL® Tissue Sealing Device by Ethicon Endo-Surgery, Inc., of Cincinnati, Ohio.

A. Exemplary Handpiece and Shaft

Figure 1:
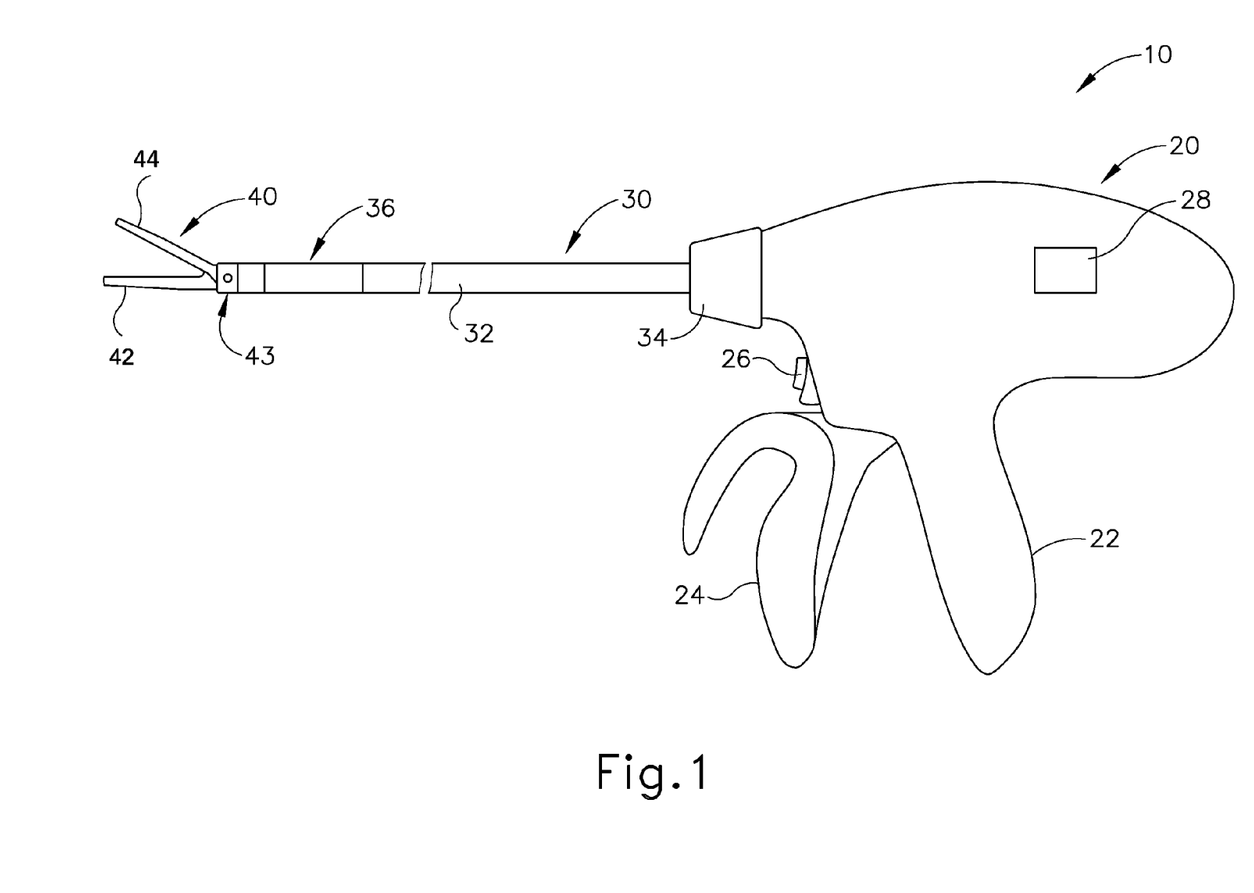
FIG. 1 depicts a side elevational view of an exemplary electrosurgical medical instrument.

Electrosurgical instrument (10) of the present example includes a handpiece (20), a shaft (30) extending distally from handpiece (20), and an end effector (40) disposed at a distal end of shaft (30). Handpiece (20) of the present example includes a pistol grip (22), a pivoting trigger (24), an activation button (26), and an articulation control (28). Trigger (24) is pivotable toward and away from pistol grip (22) to selectively actuate end effector (40) as will be described in greater detail below. Activation button (26) is operable to selectively activate RF circuitry that is in communication with end effector (40), as will also be described in greater detail below. In some versions, activation button (26) also serves as a mechanical lockout against trigger (24), such that trigger (24) cannot be fully actuated unless button (26) is being pressed simultaneously. Examples of how such a lockout may be provided are disclosed in one or more of the references cited herein. In addition or in the alternative, trigger (24) may serve as an electrical and/or mechanical lockout against button (26), such that button (26) cannot be effectively activated unless trigger (24) is being squeezed simultaneously. It should be understood that pistol grip (22), trigger (24), and button (26) may be modified, substituted, supplemented, etc. in any suitable way, and that the descriptions of such components herein are merely illustrative.

Shaft (30) of the present example includes an outer sheath (32) and an articulation section (36). Articulation section (36) is operable to selectively position end effector (40) at various angles relative to the longitudinal axis defined by sheath (32). Articulation section (36) of shaft (30) may take a variety of forms. By way of example only, articulation section (36) may be configured in accordance with one or more teachings of U.S. Pub. No. 2012/0078247, the disclosure of which is incorporated by reference herein. As another merely illustrative example, articulation section (36) may be configured in accordance with one or more teachings of U.S. Pub. No. 2012/0078248, entitled "Articulation Joint Features for Articulating Surgical Device," published Mar. 29, 2012, the disclosure of which is incorporated by reference herein. Various other suitable forms that articulation section (36) may take will be apparent to those of ordinary skill in the art in view of the teachings herein. It should also be understood that some versions of instrument (10) may simply lack articulation section (36).

In some versions, shaft (30) is also rotatable about the longitudinal axis defined by sheath (32), relative to handpiece (20), via a knob (34). Such rotation may provide rotation of end effector (40) and shaft (30) unitarily. In some other versions, knob (34) is operable to rotate end effector (40) without rotating any portion of shaft (30) that is proximal of articulation section (36). As another merely illustrative example, electrosurgical instrument (10) may include one rotation control that provides rotatability of shaft (30) and end effector (40) as a single unit; and another rotation control that provides rotatability of end effector (40) without rotating any portion of shaft (30) that is proximal of articulation section (36). Other suitable rotation schemes will be apparent to those of ordinary skill in the art in view of the teachings herein. Of course, rotatable features may simply be omitted if desired.

Articulation control (28) of the present example is operable to selectively control articulation section (36) of shaft (30), to thereby selectively position end effector (40) at various angles relative to the longitudinal axis defined by shaft (30). By way of example only, some merely illustrative forms that articulation control (28) and other components of handpiece (20) may take are disclosed in U.S. Pub. No. 2012/0078243, the disclosure of which is incorporated by reference herein; in U.S. Pub. No. 2012/0078244, entitled "Control Features for Articulating Surgical Device," published Mar. 29, 2012, the disclosure of which is incorporated by reference herein; and in U.S. patent application Ser. No. 13/622,735, now U.S. Pub. No. 2013/0023868, published Jan. 24, 2013, the disclosure of which is incorporated by reference herein. Still other suitable forms that articulation control (28) may take will be apparent to those of ordinary skill in the art in view of the teachings herein. It should also be understood that some versions of instrument (10) may simply lack an articulation control (28).

B. Exemplary End Effector

Figure 2:
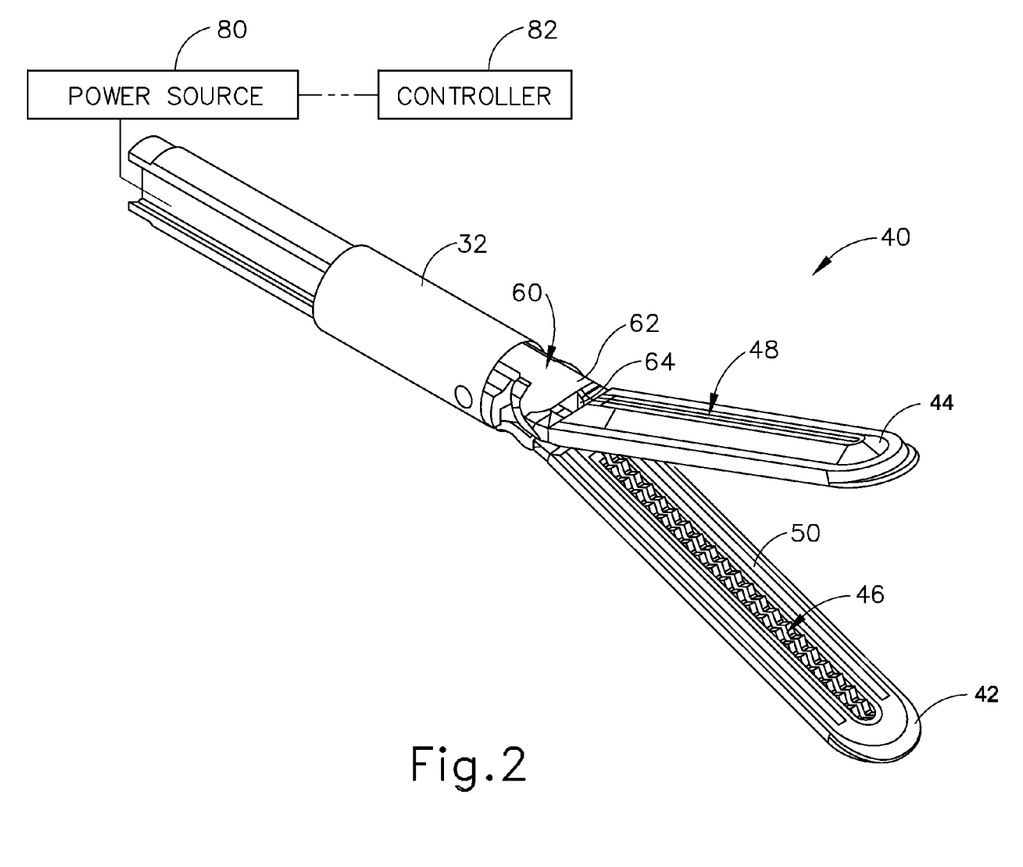
FIG. 2 depicts a perspective view of the end effector of the instrument of FIG. 1, in an open configuration.
Figure 3:
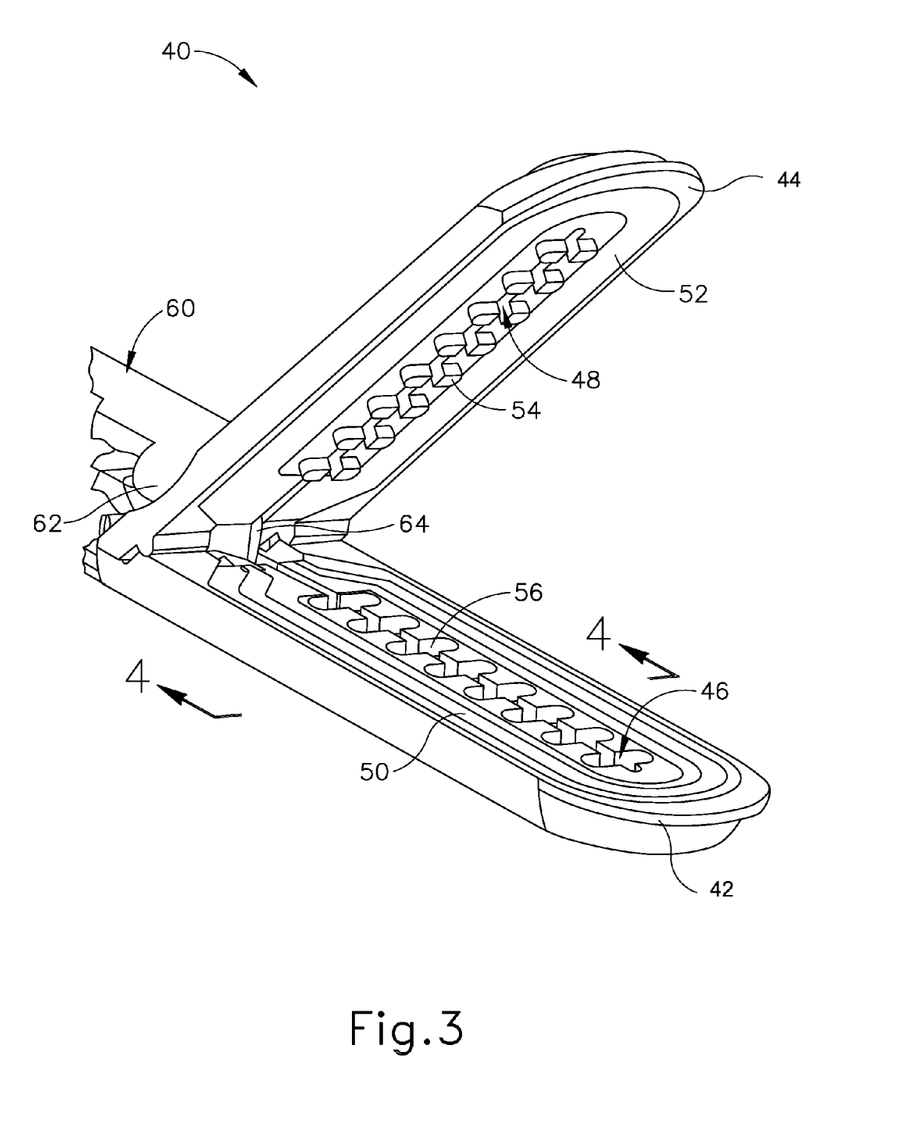
FIG. 3 depicts another perspective view of the end effector of the instrument of FIG. 1, in an open configuration.

End effector (40) of the present example comprises a first jaw (42) and a second jaw (44). In the present example, second jaw (44) is substantially fixed relative to shaft (30); while first jaw (42) pivots relative to shaft (30), toward and away from second jaw (42). In some versions, actuators such as rods or cables, etc., may extend through sheath (32) and be joined with first jaw (42) at a pivotal coupling (43), such that longitudinal movement of the actuator rods/cables/etc. through shaft (30) provides pivoting of first jaw (42) relative to shaft (30) and relative to second jaw (44). Of course, jaws (42, 44) may instead have any other suitable kind of movement and may be actuated in any other suitable fashion. By way of example only, and as will be described in greater detail below, jaws (42, 44) may be actuated and thus closed by longitudinal translation of a firing beam (60), such that actuator rods/cables/etc. may simply be eliminated in some versions.

Figure 4:
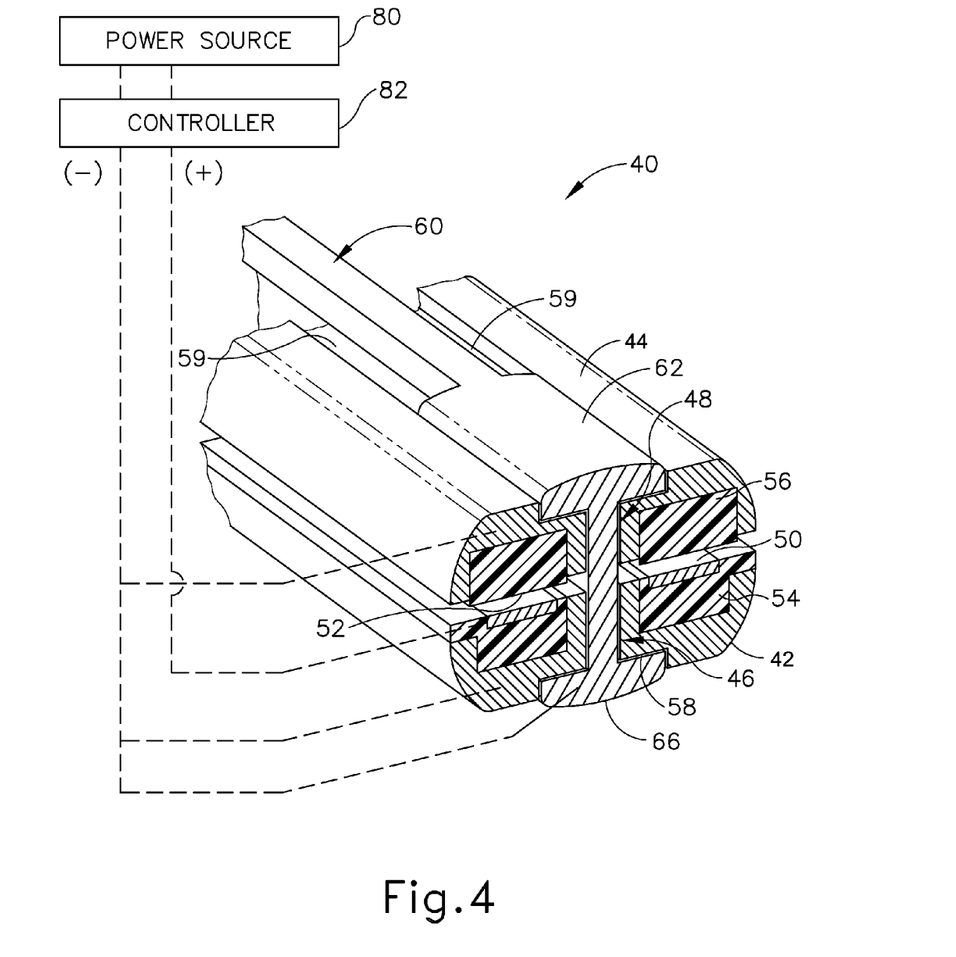
FIG. 4 depicts a cross-sectional end view of the end effector of FIG. 2, in a closed configuration and with the blade in a distal position.

As best seen in FIGS. 2-4, first jaw (42) defines a longitudinally extending elongate slot (46); while second jaw (44) also defines a longitudinally extending elongate slot (48). In addition, the top side of first jaw (42) presents a first electrode surface (50); while the underside of second jaw (44) presents a second electrode surface (52). Electrode surfaces (50, 52) are in communication with an electrical source (80) via one or more conductors (not shown) that extend along the length of shaft (30). Electrical source (80) is operable to deliver RF energy to first electrode surface (50) at a first polarity and to second electrode surface (52) at a second (opposite) polarity, such that RF current flows between electrode surfaces (50, 52) and thereby through tissue captured between jaws (42, 44). In some versions, firing beam (60) serves as an electrical conductor that cooperates with electrode surfaces (50, 52) (e.g., as a ground return) for delivery of bipolar RF energy captured between jaws (42, 44). Electrical source (80) may be external to electrosurgical instrument (10) or may be integral with electrosurgical instrument (10) (e.g., in handpiece (20), etc.), as described in one or more references cited herein or otherwise. A controller (82) regulates delivery of power from electrical source (80) to electrode surfaces (50, 52). Controller (82) may also be external to electrosurgical instrument (10) or may be integral with electrosurgical instrument (10) (e.g., in handpiece (20), etc.), as described in one or more references cited herein or otherwise. It should also be understood that electrode surfaces (50, 52) may be provided in a variety of alternative locations, configurations, and relationships.

As best seen in FIG. 4, the lower side of first jaw (42) includes a longitudinally extending recess (58) adjacent to slot (46); while the upper side of second jaw (44) includes a longitudinally extending recess (58) adjacent to slot (48). FIG. 2 shows the upper side of first jaw (42) including a plurality of teeth serrations (46). It should be understood that the lower side of second jaw (44) may include complementary serrations that nest with serrations (46), to enhance gripping of tissue captured between jaws (42, 44) without necessarily tearing the tissue. FIG. 3 shows an example of serrations (46) in first jaw (42) as mainly recesses; with serrations (48) in second jaw (44) as mainly protrusions. Of course, serrations (46, 48) may take any other suitable form or may be simply omitted altogether. It should also be understood that serrations (46, 48) may be formed of an electrically non-conductive, or insulative, material, such as plastic, glass, and/or ceramic, for example, and may include a treatment such as polytetrafluoroethylene, a lubricant, or some other treatment to substantially prevent tissue from getting stuck to jaws (42, 44).

With jaws (42, 44) in a closed position, shaft (30) and end effector (40) are sized and configured to fit through trocars having various inner diameters, such that electrosurgical instrument (10) is usable in minimally invasive surgery, though of course electrosurgical instrument (10) could also be used in open procedures if desired. By way of example only, with jaws (42, 44) in a closed position, shaft (30) and end effector (40) may present an outer diameter of approximately 5 mm. Alternatively, shaft (30) and end effector (40) may present any other suitable outer diameter (e.g., between approximately 2 mm and approximately 20 mm, etc.).

As another merely illustrative variation, either jaw (42, 44) or both of jaws (42, 44) may include at least one port, passageway, conduit, and/or other feature that is operable to draw steam, smoke, and/or other gases/vapors/etc. from the surgical site. Such a feature may be in communication with a source of suction, such as an external source or a source within handpiece (20), etc. In addition, end effector (40) may include one or more tissue cooling features (not shown) that reduce the degree or extent of thermal spread caused by end effector (40) on adjacent tissue when electrode surfaces (50, 52) are activated. Various suitable forms that such cooling features may take will be apparent to those of ordinary skill in the art in view of the teachings herein.

In some versions, end effector (40) includes one or more sensors (not shown) that are configured to sense a variety of parameters at end effector (40), including but not limited to temperature of adjacent tissue, electrical resistance or impedance of adjacent tissue, voltage across adjacent tissue, forces exerted on jaws (42, 44) by adjacent tissue, etc. By way of example only, end effector (40) may include one or more positive temperature coefficient (PTC) thermistor bodies (54, 56) (e.g., PTC polymer, etc.), located adjacent to electrodes (50, 52) and/or elsewhere. Data from sensors may be communicated to controller (82). Controller (82) may process such data in a variety of ways. By way of example only, controller (82) may modulate or otherwise change the RF energy being delivered to electrode surfaces (50, 52), based at least in part on data acquired from one or more sensors at end effector (40). In addition or in the alternative, controller (82) may alert the user to one or more conditions via an audio and/or visual feedback device (e.g., speaker, lights, display screen, etc.), based at least in part on data acquired from one or more sensors at end effector (40). It should also be understood that some kinds of sensors need not necessarily be in communication with controller (82), and may simply provide a purely localized effect at end effector (40). For instance, a PTC thermistor bodies (54, 56) at end effector (40) may automatically reduce the energy delivery at electrode surfaces (50, 52) as the temperature of the tissue and/or end effector (40) increases, thereby reducing the likelihood of overheating. In some such versions, a PTC thermistor element is in series with power source (80) and electrode surface (50, 52); and the PTC thermistor provides an increased impedance (reducing flow of current) in response to temperatures exceeding a threshold. Furthermore, it should be understood that electrode surfaces (50, 52) may be used as sensors (e.g., to sense tissue impedance, etc.). Various kinds of sensors that may be incorporated into electrosurgical instrument (10) will be apparent to those of ordinary skill in the art in view of the teachings herein. Similarly various things that can be done with data from sensors, by controller (82) or otherwise, will be apparent to those of ordinary skill in the art in view of the teachings herein. Other suitable variations for end effector (40) will also be apparent to those of ordinary skill in the art in view of the teachings herein.

C. Exemplary Firing Beam

As also seen in FIGS. 2-4, electrosurgical instrument (10) of the present example includes a firing beam (60) that is longitudinally movable along part of the length of end effector (40). Firing beam (60) is coaxially positioned within shaft (30), extends along the length of shaft (30), and translates longitudinally within shaft (30) (including articulation section (36) in the present example), though it should be understood that firing beam (60) and shaft (30) may have any other suitable relationship. Firing beam (60) includes a sharp distal blade (64), an upper flange (62), and a lower flange (66). As best seen in FIG. 4, distal blade (64) extends through slots (46, 48) of jaws (42, 44), with upper flange (62) being located above jaw (44) in recess (59) and lower flange (66) being located below jaw (42) in recess (58). The configuration of distal blade (64) and flanges (62, 66) provides an "I-beam" type of cross section at the distal end of firing beam (60). While flanges (62, 66) extend longitudinally only along a small portion of the length of firing beam (60) in the present example, it should be understood that flanges (62, 66) may extend longitudinally along any suitable length of firing beam (60). In addition, while flanges (62, 66) are positioned along the exterior of jaws (42, 44), flanges (62, 66) may alternatively be disposed in corresponding slots formed within jaws (42, 44). For instance, each jaw (42, 44) may define a "T"-shaped slot, with parts of distal blade (64) being disposed in one vertical portion of each "T"-shaped slot and with flanges (62, 66) being disposed in the horizontal portions of the "T"-shaped slots. Various other suitable configurations and relationships will be apparent to those of ordinary skill in the art in view of the teachings herein.

Distal blade (64) is substantially sharp, such that distal blade (64) will readily sever tissue that is captured between jaws (42, 44). Distal blade (64) is also electrically grounded in the present example, providing a return path for RF energy as described elsewhere herein. In some other versions, distal blade (64) serves as an active electrode. In addition or in the alternative, distal blade (64) may be selectively energized with ultrasonic energy (e.g., harmonic vibrations at approximately 55.5 kHz, etc.).

The "I-beam" type of configuration of firing beam (60) provides closure of jaws (42, 44) as firing beam (60) is advanced distally. In particular, flange (62) urges jaw (44) pivotally toward jaw (42) as firing beam (60) is advanced from a proximal position (FIGS. 1-3) to a distal position (FIG. 4), by bearing against recess (59) formed in jaw (44). This closing effect on jaws (42, 44) by firing beam (60) may occur before distal blade (64) reaches tissue captured between jaws (42, 44). Such staging of encounters by firing beam (60) may reduce the force required to squeeze trigger (24) to actuate firing beam (60) through a full firing stroke. In other words, in some such versions, firing beam (60) may have already overcome an initial resistance required to substantially close jaws (42, 44) on tissue before encountering resistance from severing the tissue captured between jaws (42, 44). Of course, any other suitable staging may be provided.

In the present example, flange (62) is configured to cam against a ramp feature at the proximal end of jaw (44) to open jaw (42) when firing beam (60) is retracted to a proximal position and to hold jaw (42) open when firing beam (60) remains at the proximal position. This camming capability may facilitate use of end effector (40) to separate layers of tissue, to perform blunt dissections, etc., by forcing jaws (42, 44) apart from a closed position. In some other versions, jaws (42, 44) are resiliently biased to an open position by a spring or other type of resilient feature. While jaws (42, 44) close or open as firing beam (60) is translated in the present example, it should be understood that other versions may provide independent movement of jaws (42, 44) and firing beam (60). By way of example only, one or more cables, rods, beams, or other features may extend through shaft (30) to selectively actuate jaws (42, 44) independently of firing beam (60). Such jaw (42, 44) actuation features may be separately controlled by a dedicated feature of handpiece (20). Alternatively, such jaw actuation features may be controlled by trigger (24) in addition to having trigger (24) control firing beam (60). It should also be understood that firing beam (60) may be resiliently biased to a proximal position, such that firing beam (60) retracts proximally when a user relaxes their grip on trigger (24).

D. Exemplary Operation

In an exemplary use, end effector (40) is inserted into a patient via a trocar. Articulation section (36) is substantially straight when end effector (40) and part of shaft (30) are inserted through the trocar. Articulation control (28) may then be manipulated to pivot or flex articulation section (36) of shaft (30) in order to position end effector (40) at a desired position and orientation relative to an anatomical structure within the patient. Two layers of tissue of the anatomical structure are then captured between jaws (42, 44) by squeezing trigger (24) toward pistol grip (22). Such layers of tissue may be part of the same natural lumen defining anatomical structure (e.g., blood veseel, portion of gastrointestinal tract, portion of reproductive system, etc.) in a patient. For instance, one tissue layer may comprise the top portion of a blood vessel while the other tissue layer may comprise the bottom portion of the blood vessel, along the same region of length of the blood vessel (e.g., such that the fluid path through the blood vessel before use of electrosurgical instrument (10) is perpendicular to the longitudinal axis defined by end effector (40), etc.). In other words, the lengths of jaws (42, 44) may be oriented perpendicular to (or at least generally transverse to) the length of the blood vessel. As noted above, flanges (62, 66) cammingly act to pivot jaw (42) toward jaw (44) when firing beam (60) is actuated distally by squeezing trigger (24) toward pistol grip (22). Jaws (42, 44) may be substantially clamping tissue before trigger (24) has swept through a full range of motion toward pistol grip (22), such that trigger (24) may continue pivoting toward pistol grip (22) through a subsequent range of motion after jaws (42, 44) have substantially clamped on the tissue.

With tissue layers captured between jaws (42, 44) firing beam (60) continues to advance distally by the user squeezing trigger (24) further toward pistol grip (22). As firing beam (60) continues to advance distally, distal blade (64) simultaneously severs the clamped tissue layers, resulting in separated upper layer portions being apposed with respective separated lower layer portions. In some versions, this results in a blood vessel being cut in a direction that is generally transverse to the length of the blood vessel. It should be understood that the presence of flanges (62, 66) immediately above and below jaws (42, 44), respectively, may help keep jaws (42, 44) in a closed and tightly clamping position. In particular, flanges (62, 66) may help maintain a significantly compressive force between jaws (42, 44). With severed tissue layer portions being compressed between jaws (42, 44), electrode surfaces (50, 52) are activated with bipolar RF energy by the user depressing activation button (26). In some versions, electrodes (50, 52) are selectively coupled with power source (80) (e.g., by the user depressing button (26), etc.) such that electrode surfaces (50, 52) of jaws (42, 44) are activated with a common first polarity while firing beam (60) is activated at a second polarity that is opposite to the first polarity. Thus, a bipolar RF current flows between firing beam (60) and electrode surfaces (50, 52) of jaws (42, 44), through the compressed regions of severed tissue layer portions. In some other versions, electrode surface (50) has one polarity while electrode surface (52) and firing beam (60) both have the other polarity. In either version (among at least some others), bipolar RF energy delivered by power source (80) ultimately thermally welds the tissue layer portions on one side of firing beam (60) together and the tissue layer portions on the other side of firing beam (60) together.

In certain circumstances, the heat generated by activated electrode surfaces (50, 52) can denature the collagen within the tissue layer portions and, in cooperation with clamping pressure provided by jaws (42, 44), the denatured collagen can form a seal within the tissue layer portions. Thus, the severed ends of the natural lumen defining anatomical structure are hemostatically sealed shut, such that the severed ends will not leak bodily fluids. In some versions, electrode surfaces (50, 52) may be activated with bipolar RF energy before firing beam (60) even begins to translate distally and thus before the tissue is even severed. For instance, such timing may be provided in versions where button (26) serves as a mechanical lockout relative to trigger (24) in addition to serving as a switch between power source (80) and electrode surfaces (50, 52). Other suitable ways in which instrument (10) may be operable and operated will be apparent to those of ordinary skill in the art in view of the teachings herein.

II. Exemplary Compliant Firing Beam

In some instances, instrument (10) may capture significantly dense and/or thick tissue between jaws (42, 44). In some such instances, flanges (62, 66) and the distal region of firing beam (60) may encounter significant stresses as firing beam (60) is advanced distally through jaws (42, 44). In particular, the stresses imposed by dense and/or thick tissue may urge flanges (62, 64) away from each other. These stresses may also spike or otherwise be inconsistent during certain stages when firing beam (60) travels through the full distal range of motion from a proximal-most position (e.g., when jaws (42, 44) are fully opened) to a distal-most position (e.g., when jaws (42, 44) are fully closed and the tissue between jaws (42, 44) has been severed by blade (64) of firing beam (60)). Such increases in stress may also provide increases in friction against firing beam (60), which may in turn require the operator to use significantly greater force in squeezing trigger (24) toward grip (26). In some instances, an operator may be unable to advance firing beam (60) through a full distal range of motion due to friction caused by significantly dense/thick tissue.

It may be desirable to provide some degree of compliance in firing beam (60) to accommodate stresses imposed by significantly dense/thick tissue. Such compliance may provide a more consistent stress on flanges (62, 66) and the distal region of firing beam (60) as firing beam (60) travels through the full distal range of motion. This may in turn provide a more consistent force profile for the operator squeezing trigger (24) toward grip (26). In addition or in the alternative, providing some degree of compliance in firing beam (60) may reduce the risk of flanges (62, 66) and/or some other portion of firing beam (60) breaking or otherwise failing when an operator misuses instrument (10) by attempting to clamp and cut tissue that is significantly dense/thick. It should be understood that a firing beam (60) may provide compliance to accommodate stresses imposed by significantly dense/thick tissue while still providing sufficient stiffness to force jaws (42, 44) to compress the tissue to enable sealing of the tissue by electrodes (50, 52).

The below discussion provides several examples of merely illustrative ways in which firing beam (60) may be modified to have some degree of compliance as jaws (42, 44) and firing beam (60) encounter significantly dense and/or thick tissue. Other suitable examples will be apparent to those of ordinary skill in the art in view of the teachings herein. It should also be understood that other portions of instrument (10) may be modified to account for compliance in firing beam (60) and/or to otherwise account for significantly dense/thick tissue. By way of example only, handpiece (20) may be modified to include a force limiting feature that prevents further advancement of firing beam (60) when the firing load on firing beam (60) exceeds a threshold. Such an overload mechanism may effectively block further pivoting of trigger (24) toward grip (22). Alternatively, such an overload mechanism may actuate a clutch that disengages trigger (24) from firing beam (60). Various suitable ways in which a firing beam (60) overload mechanism may be configured will be apparent to those of ordinary skill in the art in view of the teachings herein. Of course, such an overload mechanism is merely optional and may simply be omitted.

A. Firing Beam with Longitudinal Cutout

Figure 5:
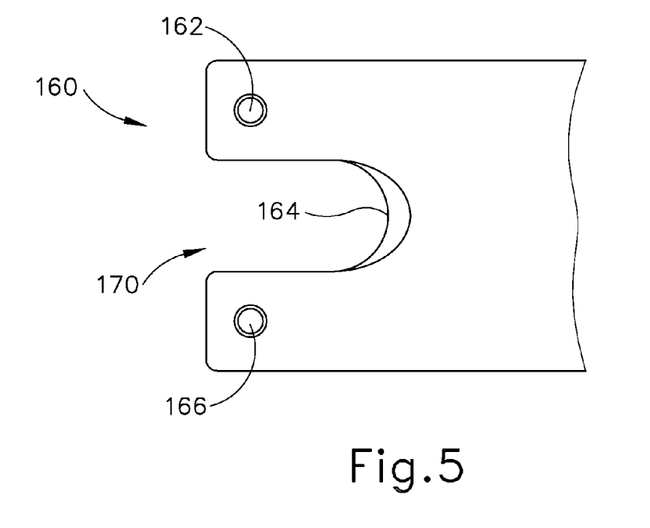
FIG. 5 depicts a side elevational view of an exemplary alternative firing beam.

FIG. 5 shows an exemplary firing beam (160) that has a longitudinally extending cutout (170). It should be understood that firing beam (60) may be readily replaced with firing beam (160). Firing beam (160) of this example includes a pair of laterally extending pins (162, 166) that are functional equivalents of flanges (62, 66). In particular, pin (162) is configured to bear down on jaw (42) as firing beam (160) is advanced distally; while pin (166) bears against jaw (44). Of course, pins (162, 166) may be substituted with flanges (62, 66) if desired. As shown, cutout (170) extends through part of the vertical region between pins (162, 166) and terminates at distal blade (164). In the present example, having cutout (170) extends through part of the vertical region between pins (162, 166) enables some degree of increased vertical displacement between pins (162, 166) when operational stresses urge pins (162, 166) away from each other.

It should be understood that the material forming firing beam (160) may provide some degree of resilient flexibility to enable vertical displacement between pins (162, 166). By way of example only, firing beam (160) may be formed of stainless steel, titanium, nitinol, etc. Other suitable materials will be apparent to those of ordinary skill in the art in view of the teachings herein. It should also be understood that firing beam (160) may be formed of two different materials, with one material being used to form the distal section of firing beam (160) (shown in FIG. 5) and another material being used to form the proximal section of firing beam (160) (not shown). Firing beam (160) may thus be formed as a multi-piece construction, with a proximal section joined to a distal section. By way of example only, such a multi-piece construction may be provided in accordance with at least some of the teachings of U.S. patent application Ser. No. 13/692,202, entitled "Surgical Instrument with Curved Blade Firing Path," filed Dec. 3, 2012, now U.S. Pat. No. 9,078,677, issued Jul. 14, 2015, the disclosure of which is incorporated by reference herein. Other suitable ways in which firing beam (160) may be constructed will be apparent to those of ordinary skill in the art in view of the teachings herein. It should also be understood that the foregoing teachings relating to firing beam (160) construction may also be readily applied to the additional examples of firing beams described below.

Figure 6:
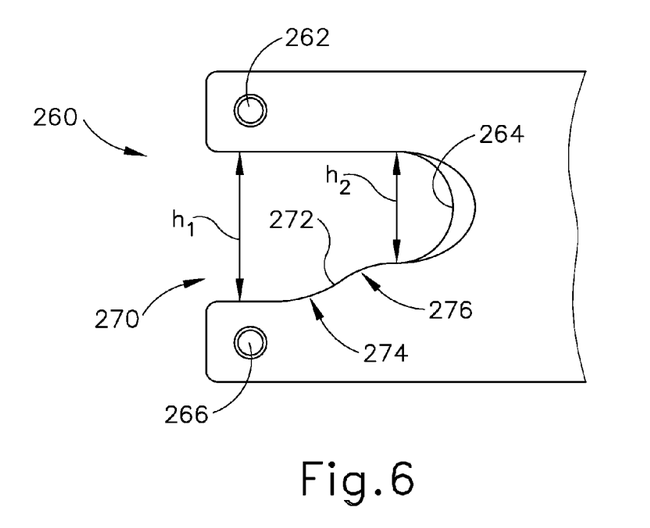
FIG. 6 depicts a side elevational view of another exemplary alternative firing beam.

FIG. 6 shows an exemplary firing beam (260) that also has a longitudinally extending cutout (270). Firing beam (260) of this example also includes a pair of laterally extending pins (262, 266), which may be considered as being interchangeable with flanges (62, 66). Cutout (270) of this example extends proximally further than cutout (170). Cutout (270) thus provides an even greater degree of compliance that may yield greater displacement between pins (262, 266) in response to stresses induced by dense/thick tissue. Cutout (270) of this example also provides a changing gap height, as compared to the constant gap height provided by cutout (170). In particular, cutout (270) provides a first gap height ($h_1$) and a second gap height ($h_2$), with first gap height ($h_1$) being greater than second gap height ($h_2$). Blade (264) thus also has a shorter height than blade (164). The two different regions of cutout (270) are separated by an obliquely angled transition region (272). A concave curve (274) provides a generally smooth transition from the distal section of cutout (270) to transition region (272); while a convex curve (276) provides a generally smooth transition from transition region (272) to the proximal section of cutout (270). It should be understood that curves (274, 276) may be replaced with corners or other features. It should also be understood that providing different gap heights ($h_1$, $h_2$) within the same cutout (270) may provided a desired degree of compliance in firing beam (260) without sacrificing too much strength in firing beam (260). Various suitable depths, heights, and other features that may be provided for cutouts (170, 270) will be apparent to those of ordinary skill in the art in view of the teachings herein.

It should also be understood that cutouts (170, 270) may be formed using a variety of techniques. By way of example only, cutouts (170, 270) may be formed using a stamping process. As another merely illustrative example cutouts (170, 270) may be formed using a laser cutting process. As yet another merely illustrative example, cutouts (170, 270) may be formed using a wire electric discharge machining (EDM) process. Alternatively, any other suitable process or combination of processes may be used to form cutouts (170, 270). It should also be understood that the foregoing teachings relating to cutout (170, 270) formation may also be readily applied to the additional examples of firing beams described below.

B. Firing Beam with Cutout and Integral Limiting Feature

Figure 7:
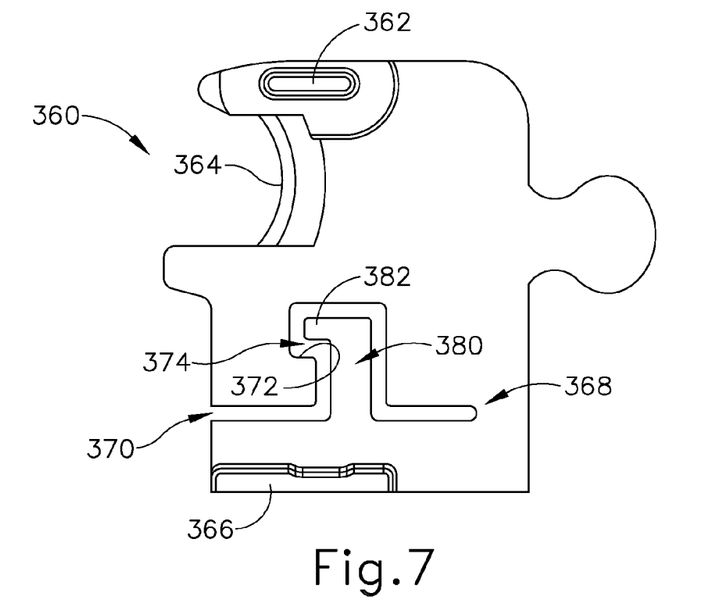
FIG. 7 depicts a side elevational view of another exemplary alternative firing beam.

In some instances, it may be desirable to provide compliance in a firing beam but still restrict the degree of compliance to a certain displacement range. FIG. 7 shows an exemplary firing beam (360) that has a cutout (370) and a displacement limiting arm (380). Firing beam (360) of this example also includes a pair of opposing, laterally extending upper flanges (362) and a pair of opposing, laterally extending lower flanges (366), with distal blade (364) being positioned between flanges (362, 366). Flanges (362, 366) may be considered as being interchangeable with flanges (62, 66). Cutout (370) of this example forms a slot that extends longitudinally, then generally vertically, then longitudinally again. Arm (380) is a unitarily formed feature of firing beam (360) and is positioned in the generally vertically extending slot portion of cutout (370). Arm (380) includes a distal projection (382) that is positioned over a shelf region (372) defined by cutout (370). When firing beam (360) is in a relaxed state (e.g., not stressed to a point of increased displacement between flanges (362, 366)), a vertical gap (374) is defined between projection (382) and shelf region (372). While projection (382) projects distally in this example, it should be understood that projection (382) may instead project proximally.

Like cutouts (170, 270) described above, cutout (370) enables some degree of increased vertical displacement between flanges (362, 366) when operational stresses urge flanges (362, 366) away from each other. In particular, a region (368) of firing beam (360) just proximal to the proximal-most point of cutout (370) acts as a living hinge. In some other versions, firing beam (360) is formed of two separate parts that are joined together by a pivoting hinge in place of the living hinge provided by region (368). As flanges (362, 366) separate from each other in response to vertically directed stresses, distal projection (382) may travel through a certain range of motion within gap (374). In some instances, projection (382) may eventually reach shelf region (372), at which point engagement between projection (382) and shelf region (372) will prevent further vertical displacement between flanges (362, 366).

In the present example, the height of gap (374) is selected to prevent plastic deformation of firing beam (360) when projection (382) travels through the full range of gap (374). Various suitable methods for determining an appropriate height for gap (374) will be apparent to those of ordinary skill in the art in view of the teachings herein. By way of example only, gap (374) may be approximately 0.020 inches. Alternatively, any other suitable height for gap (374) may be used. Similarly, other suitable longitudinal lengths and/or other suitable properties that may be provided for cutout (370) will be apparent to those of ordinary skill in the art in view of the teachings herein.

C. Firing Beam with Cutout and Resilient Insert

Figure 8:
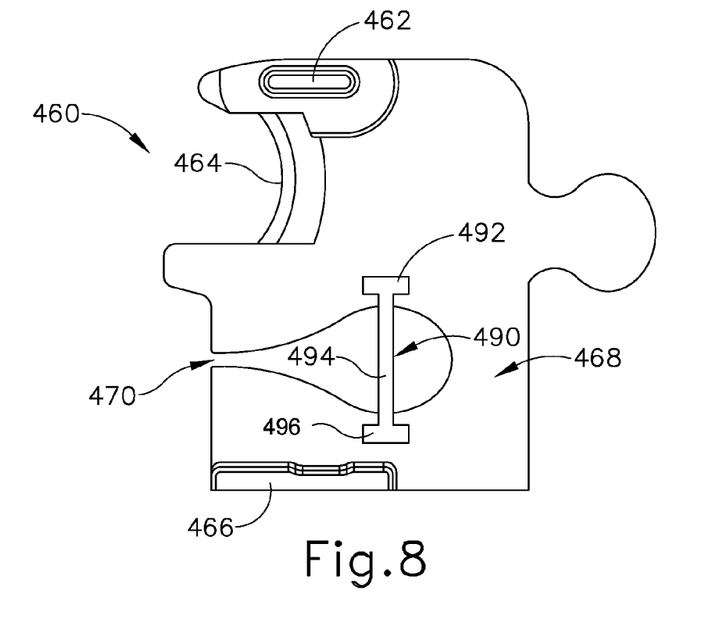
FIG. 8 depicts a side elevational view of another exemplary alternative firing beam.

In some instances, it may be desirable to introduce a component formed of a different material to alter the resilient properties of a compliant firing beam. FIG. 8 shows an exemplary firing beam (460) that has a cutout (470) and a resilient insert (490). Firing beam (460) of this example also includes a pair of opposing, laterally extending upper flanges (462) and a pair of opposing, laterally extending lower flanges (466), with distal blade (464) being positioned between flanges (462, 466). Flanges (462, 466) may be considered as being interchangeable with flanges (62, 66). Cutout (470) of this example has a teardrop shape, though it should be understood that any other suitable shape may be used. Like cutouts (170, 270, 370) described above, cutout (470) enables some degree of increased vertical displacement between flanges (462, 466) when operational stresses urge flanges (462, 466) away from each other. In particular, a region (468) of firing beam (460) just proximal to the proximal-most point of cutout (470) acts as a living hinge.

Insert (490) of the present example is shaped like an "I," with an upper flange (492) positioned at the top of a body portion (494) and a lower flange (496) positioned at the bottom of body portion (494). Flanges (492, 496) are both disposed in firing beam (460) and thereby secure insert (490) to firing beam (460). Body portion (494) extends through a gap defined by cutout (470). By way of example only, flanges (492, 496) may be pressed into firing beam (460) to provide an interference fitting. In addition or in the alternative, an adhesive and/or welding may be used to secure flanges (492) to firing beam (460). Other suitable ways in which insert (490) may be secured to firing beam (460) will be apparent to those of ordinary skill in the art in view of the teachings herein. It should also be understood that the "I" shaped configuration of insert (490) is merely illustrative; and that any other suitable configuration may be used. The cross-sectional profile of insert (490) may be selected to provide a desired degree of compliance in firing beam (460). By way of example only, insert (490) may have a "C" shape instead of an "I" shape in some other versions. Such a "C" shape may provide a greater degree of compliance than the degree of compliance provided by the "I" shape. Other suitable configurations will be apparent to those of ordinary skill in the art in view of the teachings herein.

Insert (490) may act as a plate spring and may be formed of any suitable material selected to provide a desired degree of resilience. By way of example only, insert (490) may be formed of nitinol. It should be understood that such an insert (490) may provide a constant spring rate over the full range of vertical flexure of insert (490), which may in turn yield a constant compression force against tissue clamped between jaws (42, 44) as firing beam (460) travels through a full range of distal motion. It should also be understood that insert (490) may provide a greater degree of control over the compliance of firing beam (460) than might otherwise be provided by simply having region (468) act as a living hinge. For instance, the material forming insert (490) may readily provide a desired degree of resilience that might otherwise be difficult/impractical to provide through a material desired for firing beam (460).

Figure 9:
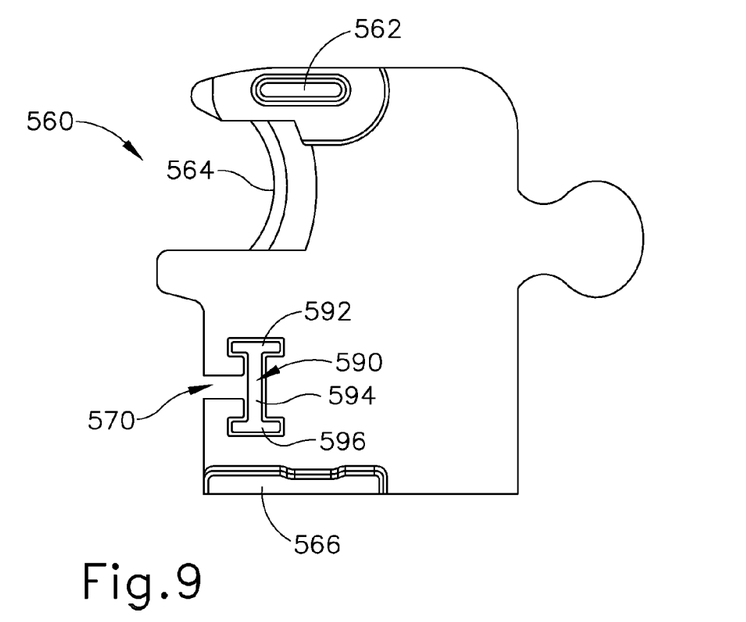
FIG. 9 depicts a side elevational view of another exemplary alternative firing beam.
Figure 10:
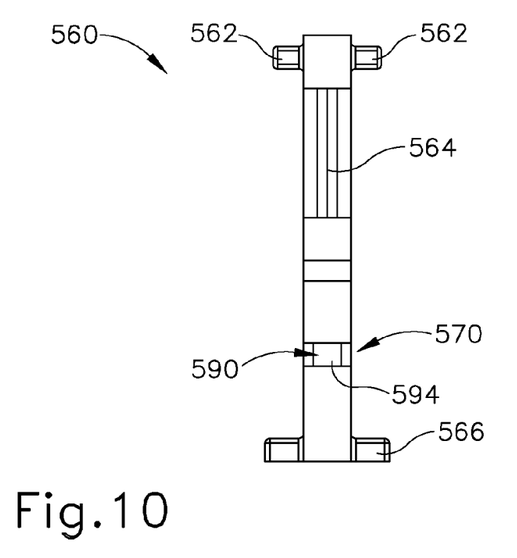
FIG. 10 depicts a front plan view of the firing beam of FIG. 9.

FIGS. 9-10 show another exemplary firing beam (560) that has a cutout (570) and a resilient insert (590). Firing beam (560) of this example also includes a pair of opposing, laterally extending upper flanges (562) and a pair of opposing, laterally extending lower flanges (566), with distal blade (564) being positioned between flanges (562, 566). Flanges (562, 566) may be considered as being interchangeable with flanges (62, 66). Cutout (570) of this example has a longitudinally extending section that terminates in an I-shaped section, with insert (590) being positioned in the I-shaped section of cutout (570). The longitudinally extending section of cutout (570) enables some degree of increased vertical displacement between flanges (562, 566) when operational stresses urge flanges (562, 566) away from each other.

Insert (590) of the present example is shaped like an "I," with an upper flange (592) positioned at the top of a body portion (594) and a lower flange (596) positioned at the bottom of body portion (594). Flanges (592, 596) are both disposed in firing beam (560) and thereby secure insert (590) to firing beam (560). By way of example only, flanges (592, 596) may be pressed into firing beam (560) to provide an interference fitting. In addition or in the alternative, an adhesive and/or welding may be used to secure flanges (592) to firing beam (560). Other suitable ways in which insert (590) may be secured to firing beam (560) will be apparent to those of ordinary skill in the art in view of the teachings herein. It should also be understood that the "I" shaped configuration of insert (590) is merely illustrative; and that any other suitable configuration may be used. Other suitable configurations will be apparent to those of ordinary skill in the art in view of the teachings herein.

Like insert (490), insert (590) may act as a plate spring and may be formed of any suitable material selected to provide a desired degree of resilience. By way of example only, insert (590) may be formed of nitinol. It should be understood that such an insert (590) may provide a constant spring rate over the full range of vertical flexure of insert (590), which may in turn yield a constant compression force against tissue clamped between jaws (42, 44) as firing beam (560) travels through a full range of distal motion. It should also be understood that the material forming insert (590) may readily provide a desired degree of resilience that might otherwise be difficult/impractical to provide through a material desired for firing beam (560).

Referring now to both examples shown in FIGS. 8-10, it should also be noted that the longitudinal positioning of insert (490, 590) may influence the compliance of firing beam (460, 560) and/or may influence the selection of material for insert (490, 590). Insert (490) is positioned proximal to the distal-most portion of flange (462) in firing beam (460); while insert (590) is positioned distal to the distal-most portion of flange (562) in firing beam (560). This positioning may tend to provide greater compliance in firing beam (460) than in firing beam (560). Other suitable positions for an insert (490, 590) will be apparent to those of ordinary skill in the art in view of the teachings herein.

Figure 11:
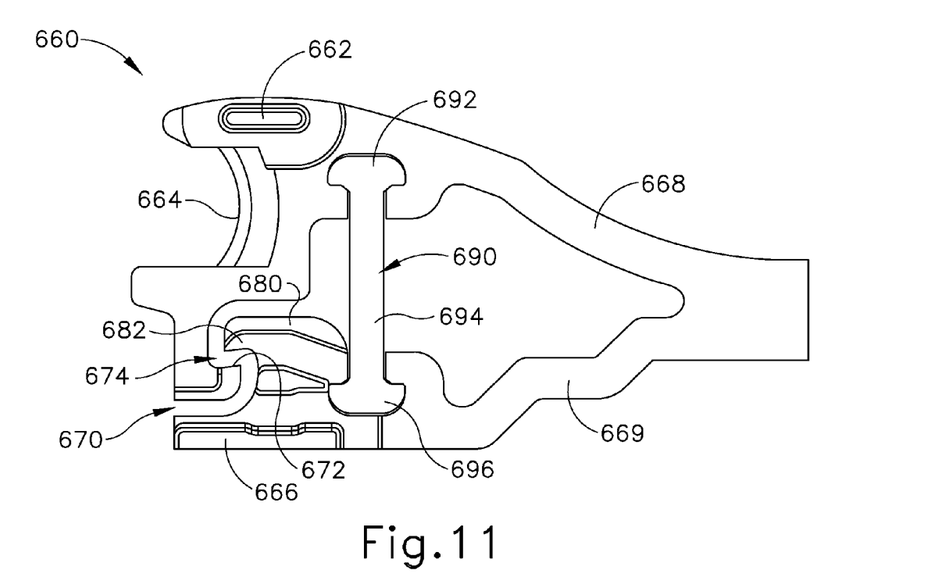
FIG. 11 depicts a side elevational view of another exemplary alternative firing beam.
Figure 12:
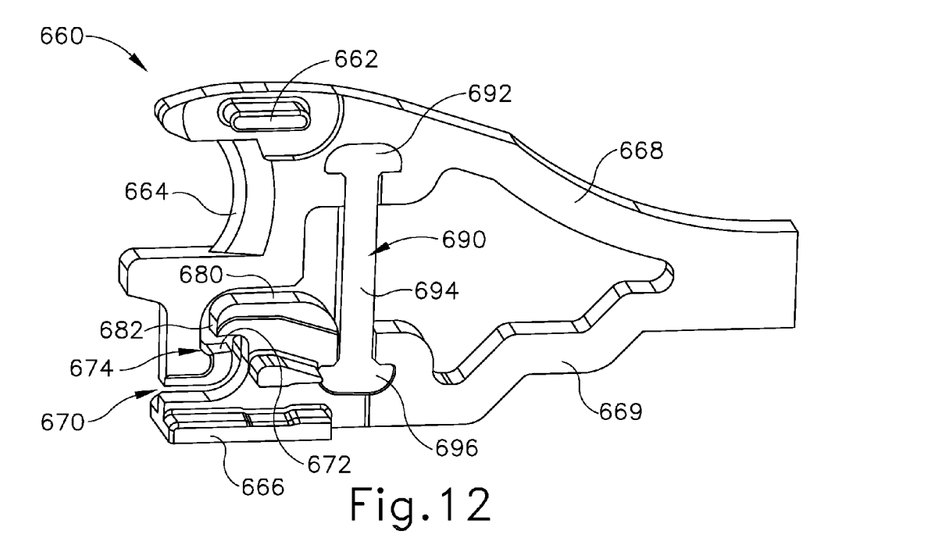
FIG. 12 depicts a perspective view of the firing beam of FIG. 11.

It should be understood that either of firing beams (460, 560) described above may also include a compliance restriction feature that restricts the degree of compliance to a certain displacement range. By way of example only, either of firing beams (460, 560) may be readily modified to include a feature similar to displacement limiting arm (380) described above. FIGS. 11-12 show an exemplary firing beam (660) that has a cutout (670), a displacement limiting arm (380), and a resilient insert (690), thus combining properties of firing beam (360) with properties of firing beams (460, 560). Firing beam (660) of this example also includes a pair of opposing, laterally extending upper flanges (662) and a pair of opposing, laterally extending lower flanges (666), with distal blade (664) being positioned between flanges (662, 666). Flanges (662, 666) may be considered as being interchangeable with flanges (62, 66).

Arm (680) is similar to arm (380) described above, and is a unitarily formed feature of firing beam (660). Arm (680) includes a distal projection (682) that is positioned over a shelf region (672) defined by cutout (670). When firing beam (660) is in a relaxed state (e.g., not stressed to a point of increased displacement between flanges (662, 666)), a vertical gap (674) is defined between projection (682) and shelf region (672). Cutout (670) enables some degree of increased vertical displacement between flanges (662, 666) when operational stresses urge flanges (662, 666) away from each other. In particular, the proximal portion of cutout (670) forms two relatively narrow elongate arms (668, 669) in firing beam (660), with arms (668, 669) being narrow enough to readily deform along a vertical plane. Such deformation of arms (668, 669) enables flanges (662, 666) to separate from each other. In the present example, both of arms (668, 669) are deformable. In some versions, one arm (668, 669) is more deformable than the other arm (668, 669). For instance, arm (668) may be more deformable than arm (669). In some other versions, one arm (668, 669) is deformable while the other arm (668, 669) is not deformable. For instance, arm (668) may be deformable while arm (669) is not deformable.

As flanges (662, 666) separate from each other in response to vertically directed stresses, distal projection (682) may travel through a certain range of motion within gap (674). In some instances, projection (682) may eventually reach shelf region (672), at which point engagement between projection (682) and shelf region (672) will prevent further vertical displacement between flanges (662, 666).

In the present example, the height of gap (674) is selected to prevent plastic deformation of firing beam (660) when projection (682) travels through the full range of gap (674). Various suitable methods for determining an appropriate height for gap (674) will be apparent to those of ordinary skill in the art in view of the teachings herein. By way of example only, gap (674) may be approximately 0.020 inches. Alternatively, any other suitable height for gap (674) may be used. Similarly, other suitable longitudinal lengths and/or other suitable properties that may be provided for cutout (670) will be apparent to those of ordinary skill in the art in view of the teachings herein.

Insert (690) of the present example is shaped like an "I," with an upper flange (692) positioned at the top of a body portion (694) and a lower flange (696) positioned at the bottom of body portion (694). Flanges (692, 696) are both disposed in firing beam (660) and thereby secure insert (690) to firing beam (660). By way of example only, flanges (692, 696) may be pressed into firing beam (660) to provide an interference fitting. In addition or in the alternative, an adhesive and/or welding may be used to secure flanges (692, 696) to firing beam (660). Other suitable ways in which insert (690) may be secured to firing beam (660) will be apparent to those of ordinary skill in the art in view of the teachings herein. It should also be understood that the "I" shaped configuration of insert (690) is merely illustrative; and that any other suitable configuration may be used. Other suitable configurations will be apparent to those of ordinary skill in the art in view of the teachings herein.

Like inserts (490, 590), insert (690) may act as a plate spring and may be formed of any suitable material selected to provide a desired degree of resilience. By way of example only, insert (690) may be formed of nitinol. It should be understood that such an insert (690) may provide a constant spring rate over the full range of vertical flexure of insert (690), which may in turn yield a constant compression force against tissue clamped between jaws (42, 44) as firing beam (660) travels through a full range of distal motion. It should also be understood that the material forming insert (690) may readily provide a desired degree of resilience that might otherwise be difficult/impractical to provide through a material desired for firing beam (660).

In some versions, firing beam (60, 360, 460, 560, 660) provides a resilient bias to position flanges (62, 362, 462, 562, 662) at an orientation that is parallel to the orientation of flanges (66, 366, 466, 566, 666). In some other versions, firing beam (60, 360, 460, 560, 660) provides a resilient bias to position flanges (62, 362, 462, 562, 662) at an orientation that is oblique relative to the orientation of flanges (66, 366, 466, 566, 666). Such a bias angle may be selectively adjusted to provide a desired stiffness. Other suitable ways in which firing beam compliance may be provided, adjusted, and/or restricted will be apparent to those of ordinary skill in the art in view of the teachings herein. Similarly, other suitable modifications that may be made to firing beams (60, 160, 260, 360, 460, 560, 660) will be apparent to those of ordinary skill in the art in view of the teachings herein.

III. Miscellaneous

It should be understood that any of the versions of electrosurgical instrument (10) described herein may include various other features in addition to or in lieu of those described above. By way of example only, any of the devices herein may also include one or more of the various features disclosed in any of the various references that are incorporated by reference herein.

It should also be understood that any of the devices described herein may be modified to include a motor or other electrically powered device to drive an otherwise manually moved component. Various examples of such modifications are described in U.S. Pub. No. 2012/0116379, entitled "Motor Driven Electrosurgical Device with Mechanical and Electrical Feedback," published May 10, 2012, now U.S. Pat. No. 9,161,803, issued Oct. 20, 2015, the disclosure of which is incorporated by reference herein. Various other suitable ways in which a motor or other electrically powered device may be incorporated into any of the devices herein will be apparent to those of ordinary skill in the art in view of the teachings herein.

It should also be understood that any of the devices described herein may be modified to contain most, if not all, of the required components within the medical device itself. More specifically, the devices described herein may be adapted to use an internal or attachable power source instead of requiring the device to be plugged into an external power source by a cable. Various examples of how medical devices may be adapted to include a portable power source are disclosed in U.S. Provisional Application Ser. No. 61/410,603, filed Nov. 5, 2010, entitled "Energy-Based Surgical Instruments," the disclosure of which is incorporated by reference herein. Various other suitable ways in which a power source may be incorporated into any of the devices herein will be apparent to those of ordinary skill in the art in view of the teachings herein.

While the examples herein are described mainly in the context of electrosurgical instruments, it should be understood that various teachings herein may be readily applied to a variety of other types of devices. By way of example only, the various teachings herein may be readily applied to other types of electrosurgical instruments, tissue graspers, tissue retrieval pouch deploying instruments, surgical staplers, surgical clip appliers, ultrasonic surgical instruments, etc. It should also be understood that the teachings herein may be readily applied to any of the instruments described in any of the references cited herein, such that the teachings herein may be readily combined with the teachings of any of the references cited herein in numerous ways. Other types of instruments into which the teachings herein may be incorporated will be apparent to those of ordinary skill in the art.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus for operating on tissue, the apparatus comprising:
   (a) a body;
   (b) a shaft extending distally from the body, wherein the shaft has a distal end;
   (c) an end effector positioned at the distal end of the shaft, wherein the end effector comprises:
      (i) a first jaw, and
      (ii) a second jaw, wherein the first jaw is operable to pivot toward the second jaw; and
   (d) a firing beam operable to translate relative to the end effector, wherein the firing beam is operable to drive the first jaw toward the second jaw, wherein the firing beam includes a deformable portion operable to deform in response to stress imposed by the end effector on the firing beam;
   wherein the deformable portion is defined in part by a cutout extending longitudinally from a distal end of the firing beam toward a proximal end of the firing beam;
   wherein the deformable portion comprises a resilient insert coupled with the firing beam, wherein the resilient insert extends between an upper and lower portion of the cutout.

2. The apparatus of claim 1, wherein the firing beam further comprises a first transverse feature operable to engage the first jaw to thereby drive the first jaw toward the second jaw.

3. The apparatus of claim 2, wherein the firing beam further comprises a second transverse feature operable to engage the second jaw.

4. The apparatus of claim 3, wherein the cutout extends between the first transverse feature and the second transverse feature.

5. The apparatus of claim 4, wherein the firing beam further comprises a compliance limiting feature operable to restrict deformation of the deformable portion.

6. The apparatus of claim 5, wherein the firing beam further comprises a shelf feature, wherein the compliance limiting feature comprises an arm having a projection positioned to travel through a gap into engagement with the shelf feature to thereby restrict deformation of the deformable portion.

7. The apparatus of claim 3, wherein the first and second transverse features comprise one or both of pins or flanges.

8. The apparatus of claim 1, wherein the deformable portion comprises a living hinge.

9. The apparatus of claim 1, wherein the resilient insert has an "I" shaped configuration with an upper flange and a lower flange, wherein the upper and lower flanges secure the resilient insert to the firing beam.

10. The apparatus of claim 1, wherein the resilient insert comprises nitinol.

11. The apparatus of claim 1, wherein the firing beam comprises a pair of elongate arms, wherein the resilient insert is positioned distal to the elongate arms.

12. The apparatus of claim 11, wherein the firing beam comprises an upper flange and a lower flange, wherein the upper and lower flanges are positioned distal to the elongate arms, wherein the upper and lower flanges are also positioned distal to the resilient insert.

13. The apparatus of claim 12, wherein the firing beam is configured to resiliently bias the upper flange and the lower flange toward non-parallel orientations relative to each other.

14. The apparatus of claim 1, wherein the body comprises a handpiece having a grip feature, wherein the end effector further comprises at least one electrode surface operable to provide RF energy to tissue.

15. An apparatus for operating on tissue, the apparatus comprising:
   (a) a body;
   (b) a shaft extending distally from the body, wherein the shaft has a distal end;
   (c) an end effector positioned at the distal end of the shaft, wherein the end effector comprises:
      (i) a first jaw, and
      (ii) a second jaw, wherein the first jaw is operable to pivot toward the second jaw; and
   (d) a firing beam operable to translate relative to the end effector, wherein the firing beam is operable to drive the first jaw toward the second jaw, wherein the firing beam comprises:
      (i) a cutout extending longitudinally from a distal end of the firing beam toward a proximal end of the firing beam,
      (ii) a pair of opposing upper and lower deformable elongate arms, wherein a portion of each of the arms is an extension of respective upper and lower portions of the cutout, wherein each of the arms is operable to deform in response to stress imposed by the end effector on the firing beam, and
      (iii) a compliance restriction feature operable to restrict deformation of the upper and lower deformable elongate arms.

16. An apparatus for operating on tissue, the apparatus comprising:
   (a) a body;
   (b) a shaft extending distally from the body, wherein the shaft has a distal end;
   (c) an end effector positioned at the distal end of the shaft, wherein the end effector comprises:
      (i) a first jaw, and
      (ii) a second jaw, wherein the first jaw is operable to pivot toward the second jaw; and (d) a firing beam operable to translate relative to the end effector, wherein the firing beam is operable to drive the first jaw toward the second jaw, wherein the firing beam comprises:
  (i) a cutout extending longitudinally from a distal end of the firing beam toward a proximal end of the firing beam,
  (ii) at least one deformable elongate arm operable to deform in response to stress imposed by the end effector on the firing beam, and
  (iii) a resilient member operable to bias the at least one deformable elongate arm to a first position, wherein the resilient member extends between an upper and lower portion of the cutout.

* * * * *